United States Patent [19]

Bellis

[11] Patent Number: 5,080,672

[45] Date of Patent: Jan. 14, 1992

[54] METHOD OF APPLYING A FULLY ALLOYED POROUS METALLIC COATING TO A SURFACE OF A METALLIC PROSTHESIS COMPONENT AND PRODUCT PRODUCED THEREBY

[76] Inventor: John Bellis, 10 Larchwood Road, Borras Park, Wrexham, Clwyd, Wales, Wales

[21] Appl. No.: 428,288

[22] Filed: Oct. 27, 1989

[30] Foreign Application Priority Data

Nov. 3, 1988 [GB] United Kingdom ............... 8825723
Jul. 31, 1989 [GB] United Kingdom ............... 8917498

[51] Int. Cl.$^5$ .................................................. A61F 2/28
[52] U.S. Cl. .................................... 623/16; 419/2; 419/8; 419/35; 419/37; 427/2; 427/190; 427/226; 427/376.8; 427/383.7; 428/312.8; 428/550
[58] Field of Search ............... 427/2, 190, 191, 226, 427/376.8, 383.7; 623/16, 16 G, 18; 419/8, 35, 37, 2; 428/312.8, 550

[56] References Cited

U.S. PATENT DOCUMENTS

| | | | |
|---|---|---|---|
| 3,855,638 | 12/1974 | Pilliar | 433/173 |
| 4,073,999 | 2/1978 | Bryan et al. | 427/376.2 |
| 4,206,516 | 6/1980 | Pilliar | 623/16 |
| 4,644,942 | 2/1987 | Sump | 427/2 |
| 4,650,109 | 3/1987 | Crivella et al. | 623/18 |
| 4,687,487 | 8/1987 | Hintermann | 623/18 |
| 4,855,101 | 8/1989 | Mohs et al. | 419/35 |

FOREIGN PATENT DOCUMENTS

| | | | |
|---|---|---|---|
| 2755762 | 7/1978 | Fed. Rep. of Germany | 623/16 G |
| 3743329 | 6/1989 | Fed. Rep. of Germany | 623/16 |
| 58-159741 | 9/1983 | Japan | 623/16 G |
| 2128501 | 5/1984 | United Kingdom | 623/16 G |

*Primary Examiner*—Shrive Beck
*Assistant Examiner*—Terry J. Owens
*Attorney, Agent, or Firm*—Kinney & Lange

[57] ABSTRACT

A fully alloyed porous metallic coating is applied to the surface of a metallic prosthetic component by producing a slurry comprising a suspension of the alloy in particulate form in a solution of water containing a film-forming binder material, applying to one or more surfaces of the component a coating of the slurry, forming concave and re-entrant depressions by pressing heat degradable spheres into the coating to promote fixation of the component when in use, heating the slurry to dry the same, and sintering the coated component to bond the particulate alloy onto the component, the spheres burning off during the subsequent heating or sintering step.

7 Claims, No Drawings

METHOD OF APPLYING A FULLY ALLOYED POROUS METALLIC COATING TO A SURFACE OF A METALLIC PROSTHESIS COMPONENT AND PRODUCT PRODUCED THEREBY

FIELD OF THE INVENTION

This invention relates to the production of coated metallic prosthetic components including orthopaedic implants.

Metallic prosthetic and orthopaedic components have been used for some considerable time for such purposes as joint reconstruction or replacement and fracture fixation. These components have been produced from a number of alloys having the required properties of biocompatibility, strength, corrosion resistance and wear resistance. In addition, prosthetic components have hitherto been provided with a porous surface for enhanced fixation.

The production of such components especially those components having porous fully alloyed surfaces, is both time consuming and expensive. Indeed, no entirely satisfactory method of producing prosthetic omponents having a porous alloyed surface of uniform thickness and properties has been found.

SUMMARY OF THE INVENTION

The present invention sets out to provide a method of applying a porous fully alloyed surface to one or more selected areas of a prosthetic component, for example an orthopaedic component, which at least alleviates many of the problems and disadvantages previously encountered.

According to the present invention in one aspect there is provided a method of applying a fully alloyed porous metallic coating to the surface of a metallic prosthetic component, the method comprising the steps of producing a slurry comprising a suspension of the alloy in particulate form in a solution of water containing a film forming binder material, applying to one or more surfaces of the component a coating of the slurry, heating the slurry coating to dry the same, and sintering the coated component to bond the particulate alloy onto the surface of the component.

The slurry coating may be applied to the component by immersing the member wholly or partially in slurry. Alternatively, the slurry may be sprayed onto the surface of the component (or a part thereof) or a cloth or mesh (e.g. a metallic mesh) impregnated with the slurry may be wrapped around the component surface.

In an alternative arrangement, the slurry is injected into a mould positioned around the component surface, the spacing between the mould and the component determining the initial thickness of the slurry coating.

The applied coating may be subjected to an initial heating step to gel the film-forming binder and to a second heating step to dry the slurry. The initial heating step may be achieved by pre-heating the component to a temperature at which the film-forming binder gels on application of the slurry coating onto the heated component surface. Alternatively, the heating step may effect both gelling and drying of the binder.

The surface of the component may be roughened initially to provide enhanced bonding for the slurry coating. This may be achieved by applying a relatively thin, initial powder coating to the component and then sintering the powder coating to bond the same onto the surface of the component.

Preferably the particulate material is a fully alloyed metallic powder of mean particle size up to 250 microns. The mean particle size of the powder may lie within the range 30-150 microns. The film-forming binder may comprise methyl cellulose, the viscosity of the slurry then preferably lying within the range 5000-25000 centipoises.

The particular material may be produced by a gas atomisation technique or by any other suitable technique, e.g. chemical or water atomisation.

The alloy is preferably a cobalt based alloy which includes chromium and molybdenum.

After gelling of the slurry and before sintering, depressions may be formed in the coating to promote fixation of the orthopaedic component when in use. The depressions are preferably generally concave and reentrant. The depressions may be formed by pressing heat degradable spheres into the gelled coating, the spheres burning off during the subsequent drying or sintering process.

According to the present invention in a further aspect there is provided a prosthetic orthopaedic component on which is formed a porous coating of a fully alloyed metallic material, the coating having been applied by one of the methods described in the preceding ten paragraphs.

DESCRIPTION OF PREFERRED EMBODIMENTS OF THE INVENTION:

The invention will now be described with reference to the following Example of a method of applying to an orthopaedic component, a porous fully alloyed coating which, in use, provides enhanced fixation.

A slurry is produced comprising a suspension of metallic powder of notional composition by weight: 27% Cr; 0.25% C; 5% Mo; 2.8% Ni; balance Co in a solution of water containing a film-forming binder material (such as methyl cellulose). A coating of this slurry is applied to a circumferential surface of a prosthetic orthopaedic component, e.g. a primary femoral component, of composition similar to that of the powder. The coating is applied to the proximal region of the component for enhanced fixation of the component in use.

Typically, the mean particle size of the metallic powder is less than 250 microns, preferably between 10 and 100 microns, for example 50 microns, and the viscosity of the slurry typically lies within the range of five thousand to twenty five thousand centipoises.

Slurries having viscosities outside of this range may, however, be used. Thus, if a non-gelling binder such as sodium carboxy methyl cellulose is employed, the viscosity of the slurry will be in excess of twenty five thousand centipoises.

The slurry coating may be applied to the surface of the component in any one of several ways. Thus, the component may be partially immersed in the slurry; alternatively, the slurry may be sprayed onto the component surface of may be applied by a suitably shaped blade or with a brush. Alternatively, particularly when an even coating of a predetermined thickness is required, the surface area of the component to be coated may be encased by a mould, the slurry being injected under pressure into the space defined between the component surface and the mould.

Typically, the thickness of the applied coating will be of the order of between 1 mm and 5 mm.

The coated component is heated at a temperature of around 50° C. to gel the methyl cellulose binder. It is then further heated to a temperature of the order of 110° C. to dry the slurry coating.

Gelling may be achieved by preheating the component to a temperature (e.g. 60° C.) at which on application of the slurry, gelling of the binder content of the slurry occurs. Where the coating is applied by an injection moulding technique, the heat may be applied to the slurry via the mould walls.

Heat degradable spheres, e.g. of polystyrene, are pressed into the gelled coating to d epth just greater than their central planes, the coating then closing partially over the exposed sphere surfaces.

The coated component is thereafter sintered in a sinter furnace at a temperature of between 1000° C. and 1500° C. to bond the metal powder to the surface of the metallic member. The sintering temperature is to a significant extent dependent upon the porosity of the coating required for the product. Thus, increases in sintering temperature produce a less porous coating.

During the drying or sintering stages the heat degradable spheres burn off to leave re-entrant generally concave depressions in the component surface. These depressions assist fixation of the component in use. If an impregnated cloth has been used to apply the coating to the member, this cloth will also burn off during sintering. If a metallic mesh is employed, then the mesh itself may form part of the final coating.

Where the slurry coating is applied by an injection moulding technique the inner mould wall may be formed with convex protrusions which produce in the gelled coating the required concave re-entrant depressions.

It is to be understood that the foregoing is merely exemplary of the invention and that modifications can readily be made thereto without departing from the true scope of the invention. Thus, the particular material may be of any suitable material, e.g. copper or copper alloys for bearing appliations; in such cases the temperatures referred to above will vary. Further, in order to achieve enhanced bonding, the surface of the component may be roughened prior to coating. This may, for example, be achieved by applying an initial relatively thin powder coating to the component.

I claim:

1. A method of applying a fully alloyed porous metallic coating to a surface of a metallic prosthesis component, the method comprising the steps of producing a slurry comprising a suspension of a metallic alloy in particulate form in a solution of water containing a film-forming binder material, applying to at least one surface of the component a coating of the slurry, forming concave and re-entrant depressions by pressing heat degradable spheres into the coating to promote fixation of the component when in use, heating the slurry coating to dry the same, and sintering the coated component to bond the particulate alloy onto the component, the spheres burning off during the subsequent heating or sintering step.

2. A method as claimed in claim 1, wherein, to enhance bonding of the metallic coating to the component, a thin, initial powder coating is applied to the surface of the component prior to applying the coating of the slurry to the surface of the component.

3. A method as claimed in claim 1 wherein the particulate alloy is a fully alloyed metallic powder of mean particle size no greater than 250 microns.

4. A method as claimed in claim 1 wherein the alloy is a cobalt based alloy which includes chromium and molybdenum.

5. A method as claimed in claim 1 wherein the slurry is applied to the at least one surface of the component by injecting the slurry into a mold positioned around the component surface to be coated, the spacing between the mold and the component determining the initial thickness of the slurry coating.

6. A method as claimed in claim 1 wherein he component is preheated to a temperature at which the film-forming binder gels on application of the slurry component onto the heated component surface.

7. A prosthetic component on which is formed a porous coating of a fully alloyed metallic material, the coating having been applied by a method as claimed in claim 1.

* * * * *

UNITED STATES PATENT AND TRADEMARK OFFICE
CERTIFICATE OF CORRECTION

PATENT NO. : 5,080,672
DATED : January 14, 1992
INVENTOR(S) : John Bellis

It is certified that error appears in the above-identified patent and that said Letters Patent is hereby corrected as shown below:

Col. 4, line 35, delete "he" and insert --the--

Signed and Sealed this

Sixth Day of April, 1993

Attest:

STEPHEN G. KUNIN

*Attesting Officer*  *Acting Commissioner of Patents and Trademarks*